United States Patent
Moritsugu et al.

(10) Patent No.: US 12,099,039 B2
(45) Date of Patent: Sep. 24, 2024

(54) METHOD FOR EVALUATING EMBRITTLEMENT OF AMORPHOUS ALLOY RIBBON AND TEST DEVICE FOR EVALUATING EMBRITTLEMENT OF AMORPHOUS ALLOY RIBBON

(71) Applicant: PROTERIAL, LTD., Tokyo (JP)

(72) Inventors: Nakao Moritsugu, Tokyo (JP); Hiroshi Takashima, Tokyo (JP)

(73) Assignee: PROTERIAL, LTD., Tokyo (JP)

( * ) Notice: Subject to any disclaimer, the term of this patent is extended or adjusted under 35 U.S.C. 154(b) by 0 days.

(21) Appl. No.: 17/581,262

(22) Filed: Jan. 21, 2022

(65) Prior Publication Data

US 2022/0236158 A1 Jul. 28, 2022

(30) Foreign Application Priority Data

Jan. 26, 2021 (JP) .................................. 2021-009942
Jan. 26, 2021 (JP) .................................. 2021-009943
Sep. 24, 2021 (JP) .................................. 2021-154980

(51) Int. Cl.
| | | |
|---|---|---|
| *G01N 3/28* | (2006.01) | |
| *C22C 45/02* | (2006.01) | |
| *G01N 3/02* | (2006.01) | |
| *G01N 3/08* | (2006.01) | |
| *G01N 3/42* | (2006.01) | |
| *G01N 19/08* | (2006.01) | |
| (Continued) | | |

(52) U.S. Cl.
CPC .............. *G01N 3/28* (2013.01); *C22C 45/02* (2013.01); *G01N 3/02* (2013.01); *G01N 33/20* (2013.01)

(58) Field of Classification Search
CPC .. G01N 3/08; G01N 3/28; G01N 3/02; G01N 33/20; B32B 15/01; C22C 19/07; C22C 45/02; C22C 33/003; C21D 9/52; C21D 6/008; B23K 35/3033; B22D 11/06; B22D 11/00; H01F 1/15308
See application file for complete search history.

(56) References Cited

U.S. PATENT DOCUMENTS

| | | |
|---|---|---|
| 2008/0010031 A1 | 1/2008 | Kim et al. |
| 2011/0174036 A1 | 7/2011 | Mauvoisin |
| | (Continued) | |

FOREIGN PATENT DOCUMENTS

| | | | | |
|---|---|---|---|---|
| CN | 106483021 A | * | 3/2017 | ............... G01N 3/08 |
| DE | 102012100639 A1 | * | 8/2012 | ............... G01N 3/42 |
| WO | 2019009309 A1 | | 1/2019 | |

OTHER PUBLICATIONS

Extended European Search Report issued for the corresponding European Patent Application No. 22152965.4, dated Jun. 13, 2022.
(Continued)

*Primary Examiner* — Brandi N Hopkins
(74) *Attorney, Agent, or Firm* — Meunier Carlin & Curfman LLC

(57) ABSTRACT

A new method for evaluating embrittlement of an amorphous alloy ribbon is provided. The method includes: pressing a pressurization member from one side to a plurality of positions of an amorphous alloy ribbon; scattering, in the amorphous alloy ribbon, pressurization portions where the pressurization member is pressed to form indentation; and evaluating embrittlement by the number or distribution of pressurization portions where cracks have occurred.

19 Claims, 8 Drawing Sheets

(51) Int. Cl.
*G01N 21/59* (2006.01)
*G01N 33/20* (2019.01)

(56) References Cited

U.S. PATENT DOCUMENTS

| | | | |
|---|---|---|---|
| 2019/0293536 A1* | 9/2019 | Hamaki | C01B 32/26 |
| 2020/0225134 A1* | 7/2020 | Jeong | G01N 3/20 |
| 2021/0310097 A1 | 10/2021 | Azuma et al. | |

OTHER PUBLICATIONS

Metlab Corporation: "MetLab Corporation" Dec. 31, 2018, 56 pages.
Office Action issued in counterpart European Application No. 22152965.4, dated May 14, 2024.
ASTM E384-22: "Standard Test Method for Microindentation Hardness of Materials", ASTM International, Oct. 1, 2022 (Oct. 1, 2022), pp. 1-40, XP093160117 DOI: 10.1520/E0384-22.
ASTM C730-98: "Standard Test Method for Knoop Indentation Hardness of Glass", Jan. 1, 2021 (Jan. 1, 2021), pp. 1-5, XP093160128, West Conshohocken, PA DOI: 10.1520/C0730-98R21.

* cited by examiner

METHOD FOR EVALUATING EMBRITTLEMENT OF AMORPHOUS ALLOY RIBBON AND TEST DEVICE FOR EVALUATING EMBRITTLEMENT OF AMORPHOUS ALLOY RIBBON

CROSS-REFERENCE TO RELATED APPLICATIONS

The present application claims the benefits of Japanese Patent Application No. 2021-009942 and Japanese Patent Application No. 2021-009943 filed to Japanese Patent Office on Jan. 26, 2021, and Japanese Patent Application No. 2021-154980 filed to Japanese Patent Office on Sep. 24, 2021, the disclosure content of which is incorporated herein by reference.

BACKGROUND

The present disclosure relates to a method for evaluating embrittlement of an amorphous alloy ribbon and a test device for evaluating embrittlement of an amorphous alloy ribbon.

A ribbon-shaped amorphous alloy obtained by continuously casting a molten metal adjusted to an appropriate composition under a cooling condition of about $10^{6 \circ}$ C./sec by single-roll rapid-quenching solidification processing or the like is known. The amorphous alloy is long and excellent in magnetic property, and is employed as a magnetic material for a magnetic core used in transformers, reactors, filters, motors, and the like.

The atomic structure of an amorphous alloy is ideally in an amorphous state as a whole. On the other hand, the amorphous alloy ribbon may have a part that is not cooled at an appropriate speed due to various factors in the manufacturing process such as surface scratches on the cooling roll, unevenness on the cooling roll surface due to adhesion of foreign matters, and non-uniformity of temperature distribution of the cooling roll, and some parts may crystallize. Partial fluctuations in the alloy composition may occur in the amorphous alloy ribbon also due to the influence of impurities contained in the alloy. Such an amorphous alloy ribbon tends to be embrittled, and even if a predetermined magnetic property is obtained, there is a problem that the strength is weakened at the embrittled part.

It is known that a tearing test is used to evaluate embrittlement of amorphous alloy ribbons. Specifically, there is an evaluation method specified as strip tear brittleness (strip tear ductility) in JIS C2534 (2017) and IEC60404-8-11. In these evaluation methods/tests, a test piece (sample) of a certain length (length twice the circumference of the casting roll) is obtained from a long amorphous alloy ribbon, and the test piece is torn in the casting direction of the amorphous alloy ribbon, divided by the number of brittle spots to be generated, and evaluated. The brittle spot is defined as a region where damage in dimensions greater than about 6 mm such as a crevice path, a directional change, and broken piece separation, when the test piece is torn. The property of strip tear brittleness is divided into five stages by the number of brittle spots. It is specified that the test piece is torn in a direction parallel to the casting direction at five points of 12.7 mm and 25.4 mm in the width direction from the edge and the center of the width direction, and the number of brittle spots in one test piece does not exceed 10.

The amorphous alloy ribbon is sometimes provided to the market as it is in primary processing by casting, or provided to the market in a state of being subjected to additional processing such as cutting off the edge portion of the ribbon in the width direction and cutting to a predetermined width dimensions and length so that it is easily handled during transportation or the like. In general, those having been subjected to secondary processing such as cutting and punching using them are used for the magnetic core. Hereafter, for easy explanation, the amorphous alloy ribbon before subjected to secondary processing is called the as-cast ribbon to distinguish it.

It is known that a brittle as-cast ribbon has a problem of cuttability, such as a crevice occurring at an edge part of the amorphous alloy ribbon and breaking of the ribbon due to a cutting process. Therefore, as disclosed in International Publication No. 2019/009309 and the like, the embrittlement evaluation by the tearing test is sometimes used as an index of cuttability of the amorphous alloy ribbon (as-cast ribbon).

SUMMARY

Evaluating the degree of embrittlement of the amorphous alloy ribbon by a tearing test is useful for subjecting the selected as-cast ribbon to secondary processing and reducing the occurrence of breakage when dividing in the same direction as the direction of cutting. However, the tearing test has a restriction in the lower limit of the width dimension of the sample to be tested due to the specification of the tear position, and the broader the sample is, the more likely it is that the embrittlement portion is overlooked.

In a case where the as-cast ribbon is continuously punched at a narrow pitch or punched into a complicated shape or a wide width, or in a case where the as-cast ribbon is cut at a narrow pitch in a direction different from the casting direction, it is required to evaluate the condition of the embrittlement in more detail. However, since the tearing test is a simple evaluation method, it is difficult to examine more closely the degree of embrittlement, embrittlement sites, and the distribution thereof. In response to such demand, no proposal has been made for a new evaluation method different from the tearing test, and no test device used for the evaluation has been provided.

Therefore, in the present disclosure, it is desirable to provide a new method for evaluating the embrittlement of an amorphous alloy ribbon, or to provide a test device used for the new method for evaluating the embrittlement of an amorphous alloy ribbon.

The present disclosure includes the following configuration.

<1> A method for evaluating embrittlement of an amorphous alloy ribbon, the method including: pressing a pressurization member from one side to a plurality of positions of an amorphous alloy ribbon, scattering, in the amorphous alloy ribbon, pressurization portions where the pressurization member is pressed to form indentation, and evaluating embrittlement by the number or distribution of pressurization portions where cracks have occurred.

<2> The method for evaluating embrittlement of an amorphous alloy ribbon according to <1>, in which an elastic member is placed on a side opposite to the surface on which the pressurization member of the amorphous alloy ribbon is pressed, and the pressurization member is pressed.

<3> The method for evaluating embrittlement of an amorphous alloy ribbon according to <1> or <2>, in which the amorphous alloy ribbon is magnetically adsorbed and fixed, and the pressurization member is pressed.

<4> The method for evaluating embrittlement of an amorphous alloy ribbon according to any one of <1> to <3>, in which a crack is discriminated by discontinuity of waviness of a surface shape of the pressurization portion.

<5> The method for evaluating embrittlement of an amorphous alloy ribbon according to any one of <1> to <3>, in which a crack is discriminated from a light transmission state of the pressurization portion.

<6> The method for evaluating embrittlement of an amorphous alloy ribbon according to any one of <1> to <3>, in which a crack is discriminated by a decrease change in pressurization force of the pressurization member.

<7> A test device for evaluating embrittlement of an amorphous alloy ribbon, the test device including a measurement table including a plane on which an amorphous alloy ribbon is placed, and a pressurization means for pressing a pressurization member from one side to a plurality of positions of the amorphous alloy ribbon and scattering, in the amorphous alloy ribbon, pressurization portions where the pressurization member is pressed to form indentation.

<8> The test device for evaluating embrittlement of an amorphous alloy ribbon according to <7>, in which the pressurization means can form a crack in at least one of a plurality of the pressurization portions.

<9> The test device for evaluating embrittlement of an amorphous alloy ribbon according to <7> or <8>, in which the pressurization means is positioned above a plane of the measurement table and can move in a substantially perpendicular direction with respect to a plane of the measurement table.

<10> The test device for evaluating embrittlement of an amorphous alloy ribbon according to any one of <7> to <9>, in which the pressurization member is a rod-shaped member, and the pressurization member is moved in a substantially perpendicular direction with respect to a plane of the measurement table to pressurize the amorphous alloy ribbon with a tip end side of the pressurization member.

<11> The test device for evaluating embrittlement of an amorphous alloy ribbon according to <10>, in which the tip end side of the pressurization member is curved or pyramid.

<12> The test device for evaluating embrittlement of an amorphous alloy ribbon according to any one of <7> to <11>, the test device including a magnetic adsorbent device for fixing the amorphous alloy ribbon to the measurement table.

<13> The test device for evaluating embrittlement of an amorphous alloy ribbon according to any one of <7> to <12>, in which the pressurization means includes a load sensor.

<14> The test device for evaluating embrittlement of an amorphous alloy ribbon according to <13>, the test device that is configured to be able to detect a crack in the amorphous alloy ribbon from pressurization force information obtained based on an electric signal from the load sensor.

EFFECTS OF THE INVENTION

According to the present disclosure, it is possible to provide a new method for evaluating embrittlement of an amorphous alloy ribbon. According to the present disclosure, it is possible to provide a test device used for a new method for evaluating embrittlement of an amorphous alloy ribbon.

BRIEF DESCRIPTION OF THE DRAWINGS

Embodiments of the present disclosure will be described hereinafter by way of example with reference to the accompanying drawings, in which.

DETAILED DESCRIPTION OF EXEMPLARY EMBODIMENTS

Figure 1:
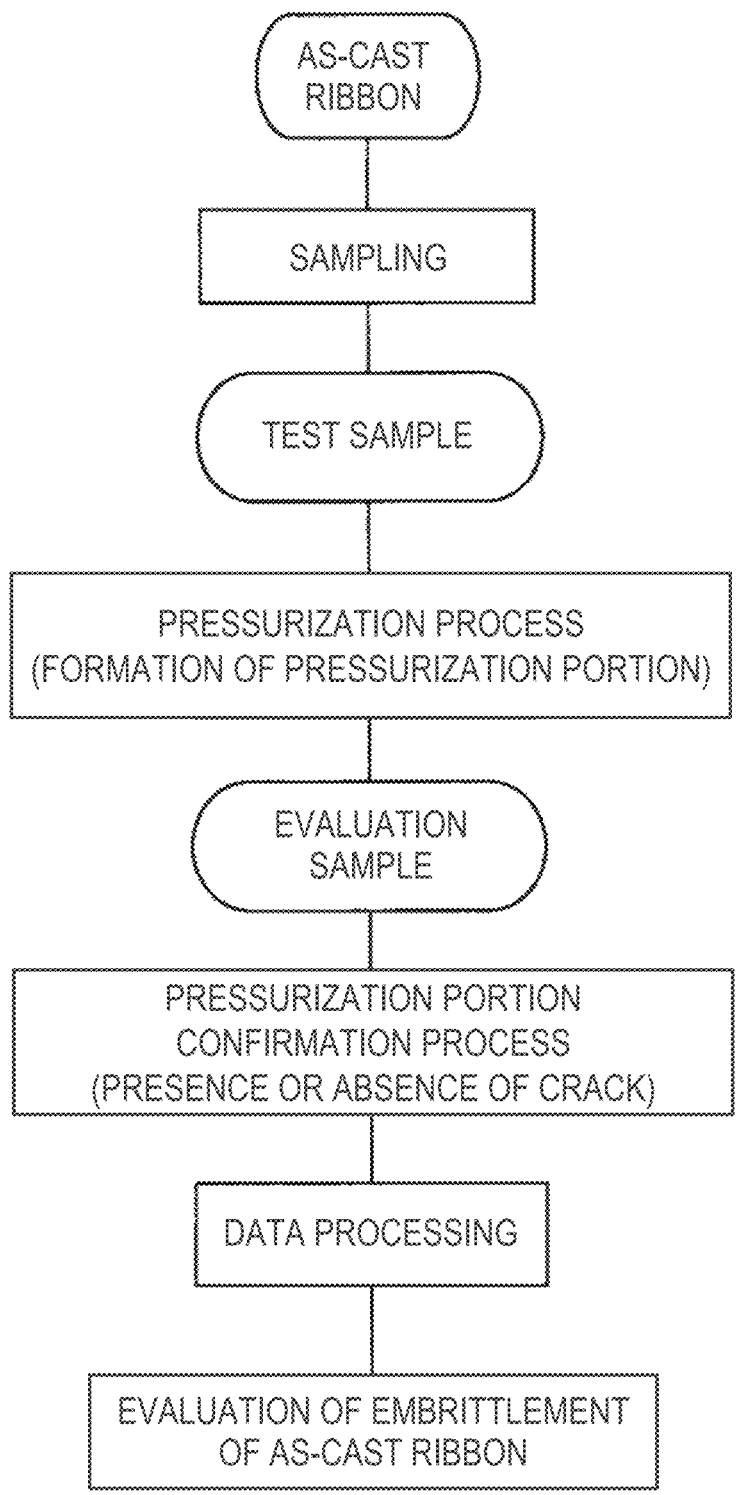
FIG. 1 is a flowchart showing an example of a method for evaluating embrittlement of an amorphous alloy ribbon of the present disclosure.

Preferred embodiments of the present disclosure will be described with reference to the drawings. The present disclosure is not necessarily limited to the embodiments described below, and unless otherwise specified, includes alternatives and modifications included in the scope of claims. In the drawings to be referred to, the same reference numerals indicate the same elements, and redundant contents may be omitted as appropriate in the description.

The method for evaluating embrittlement of an amorphous alloy ribbon of the present disclosure is a method including: pressing a pressurization member from one side to a plurality of positions of an amorphous alloy ribbon, scattering, in the amorphous alloy ribbon, pressurization portions where the pressurization member is pressed to form indentation, observing a crack in the pressurization portion, and evaluating embrittlement by the number or distribution of pressurization portions where cracks have occurred.

FIG. 1 is a flowchart showing an embodiment of a method for evaluating embrittlement of an amorphous alloy ribbon. In a method for evaluating embrittlement of an amorphous alloy ribbon (hereinafter referred to as an embrittlement evaluation method) newly proposed by the present inventors, in a pressurization process where an amorphous alloy ribbon (hereinafter referred to as a sample) having a predetermined dimension obtained from an as-cast ribbon, for example, is used to press a pressurization member against the sample to form a pressurization portion, the sample is pressurized to an extent where indentation occurs from one side so as to partially deform the sample, and the sample in which a plurality of pressurization portions are formed with predetermined intervals are created. In the following description, the sample before pressurization is called a test sample, and the sample after pressurization is called an evaluation sample to distinguish them, but the reference numerals given to the samples are the same. The amorphous alloy ribbon for which embrittlement is evaluated is not limited to an as-cast ribbon, and may be a secondary processed amorphous alloy ribbon, or the secondary processed amorphous alloy ribbon may be evaluated as a sample as it is, and a sample may be cut out from the secondary processed amorphous alloy ribbon and evaluated.

In the next pressurization portion confirmation process, an occurrence of a crack in the pressurization portion is confirmed using an obtained evaluation sample. In the pressurization process, a force (also referred to as a pressurization force) applied to the test sample for the purpose of evaluating embrittlement is set so that a pressurization portion with a crack and a pressurization portion without a crack are mixed in a plurality of pressurization portions formed in a test sample. By pressurization portion formation over the entire plane of the region where embrittlement is evaluated in the test sample, it is possible to evaluate embrittlement of the amorphous alloy ribbon by using the number (degree of embrittlement) of pressurization portions where cracks have occurred and the distribution (embrittlement points) of pressurization portions where cracks have occurred. Although the details will be described later, it is also possible, from pressurization force information obtained in the pressurization portion formation, to determine the presence or absence of occurrence of a crack in the pressurization portion by detecting change in the pressurization force information, and perform a crack inspection process together with the pressurization process.

The composition of the amorphous alloy ribbon of the present disclosure is not particularly limited, but for example, there are an alloy ribbon having a composition of Fe—Si—B-based, known as METGLAS (registered trademark) 2605SA1 material or 2605HB1M material, and alloy ribbons having compositions such as Fe—Si—B—C-based and Fe—Si—B—C—Cr-based that contain other elements. The amorphous alloy ribbon may be an alloy ribbon that can be nanocrystallized by heat treatment. For example, there are alloy ribbons having a composition of Fe—Si—B—Cu—Nb-based, known as FINEMET (registered trademark), and alloy ribbons having other compositions such as Fe—Cu—Si—B-based, Fe—Cu—B-based, and Fe—Ni—Cu—Si—B-based. As for these amorphous alloy ribbons, alloy ribbons having a thickness of 10 to 40 μm and a width of 50 mm to 220 mm are available.

When evaluating embrittlement of the as-cast ribbon, the test sample is preferably obtained from the full width of the as-cast ribbon and a continuous portion having a constant length. The constant length is preferably equal to or greater than a circumference length of a casting roll in continuous casting, for example, typically a length of equal to or greater than 1 m, and it may be used as a test sample as a whole, or may be used as a test sample after dividing into a predetermined dimensions. The size of the test sample is not particularly limited as long as it can be placed on the stage of the device described later, and the pressurization portion can be formed. The preferred upper limit dimension is specified by the width dimension of the amorphous alloy ribbon. The lower limit dimension is preferably determined in consideration of the tip end dimension of the pressurization member, the intervals between the pressurization portions, and the like, which will be described later. It is typically rectangular or square and has dimensions of 10 mm to 250 mm in width and 10 mm to 250 mm in length. Preferably, the width is equal to or greater than 20 mm and the length is equal to or greater than 20 mm, and more preferably, the width is equal to or greater than 30 mm and the length is equal to or greater than 30 mm.

When evaluating embrittlement of an amorphous alloy ribbon different from the as-cast ribbon, the amorphous alloy ribbon may be evaluated by using, as it is as a test evaluation sample, the amorphous alloy ribbon to be evaluated, or the amorphous alloy ribbon may be evaluated by taking out a test sample from the amorphous alloy ribbon to be evaluated.

Figure 2:
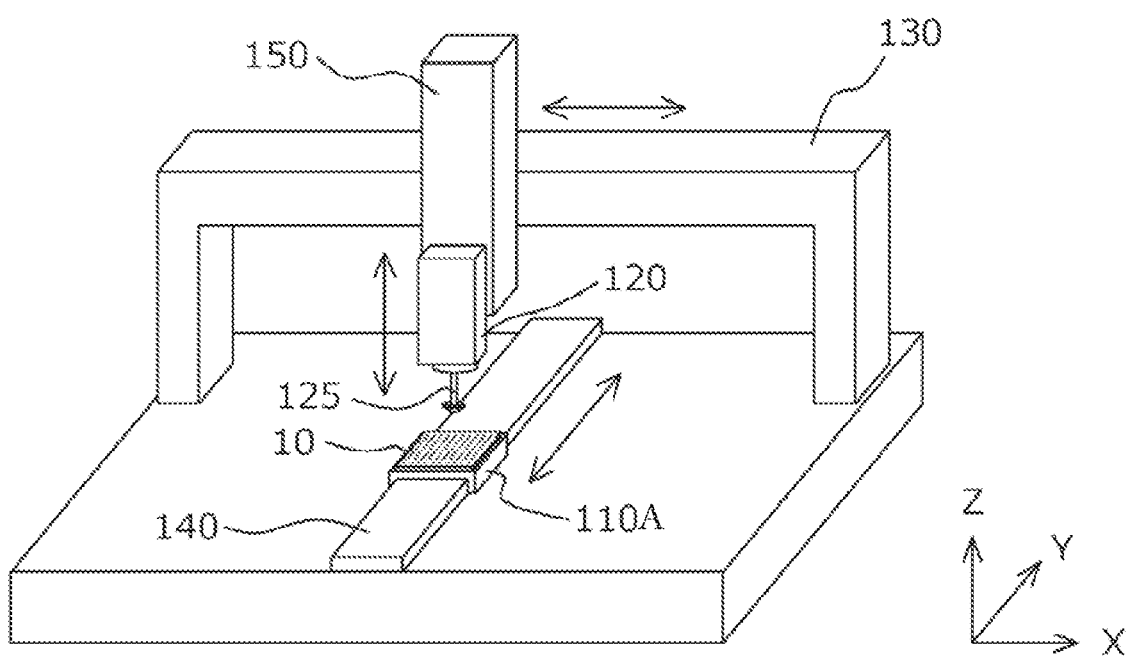
FIG. 2 is a schematic view showing an example of an outline configuration of a device used for evaluating embrittlement of the amorphous alloy ribbon of the present disclosure.
Figure 3:
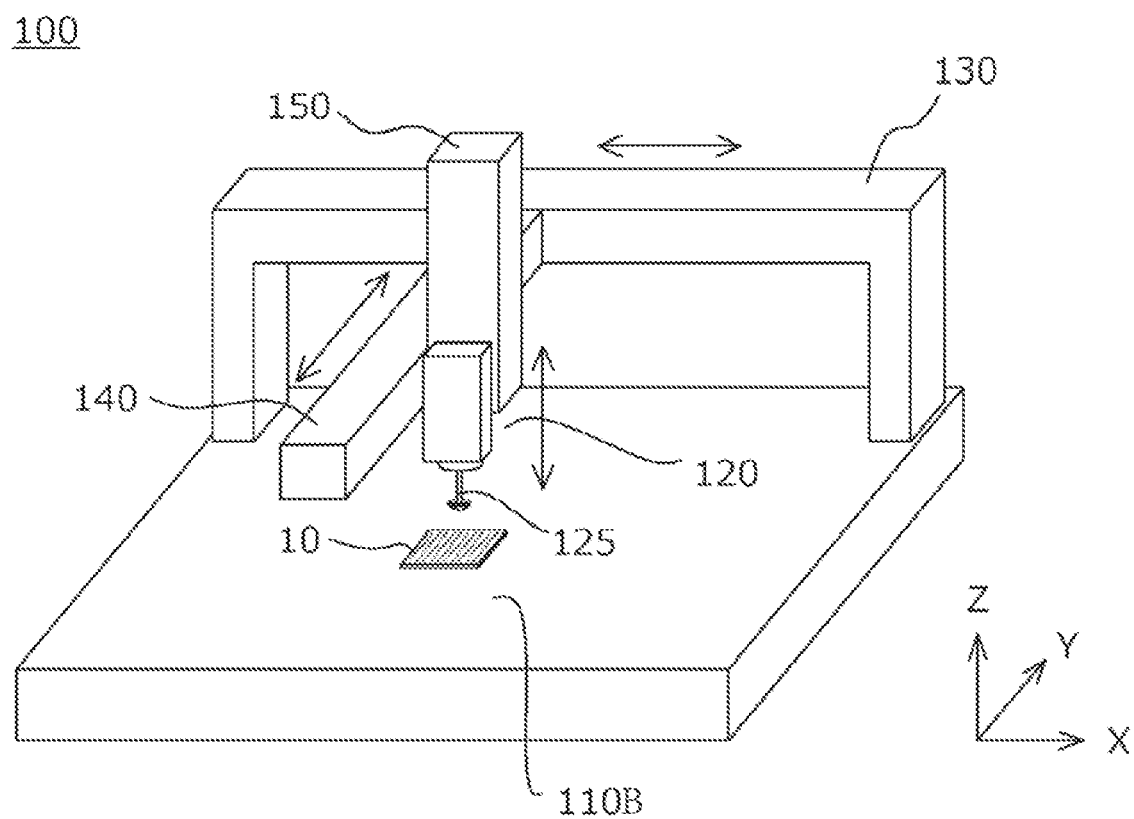
FIG. 3 is a schematic view showing another example of an outline configuration of a device used for evaluating embrittlement of the amorphous alloy ribbon of the present disclosure.

The embrittlement evaluation method and the test device used for it will be described in detail. FIGS. 2 and 3 are schematic views showing an outline configuration of a test device used for embrittlement evaluation. An example of the configuration of a test device 100 of the present disclosure includes a stage 110 (e.g., the stages 110A and 110B) having a plane on which at least a test sample 10 can be placed, and a pressurization means (a pressurization device) that is positioned above the stage 110 and can pressurize in a substantially perpendicular direction with respect to the plane of the test sample 10 placed on the stage 110.

The test device 100 illustrated in FIG. 2 includes an X-axis direction drive unit 130 and a Z-axis direction drive unit 150 for moving the position of the pressurization means, and a Y-axis direction drive unit 140 for moving the stage 110A, and the pressurization means can be relatively moved to an arbitrary position on the test sample 10 by using them as movement means. As shown in FIG. 3, the test device 100 may be a test device in which the pressurization means is moved by the X-axis direction drive unit 130, the Y-axis direction drive unit 140, and the Z-axis direction drive unit 150 without using the stage 110B as a movable stage, and the test sample 10 is stationary on the stage 110B.

Each of the drive units 130, 140, and 150 has a stepping motor or servo (pulse) motor not illustrated, a ball screw, and a linear guide, and preferably includes an encoder for position detection.

The pressurization means positioned above the test sample 10 placed on the stage 110 of the test device 100 has a pressurization member 125 that can pressurize the test sample 10 to form indentation.

The pressurization member 125 preferably has a rod-like structure, has rigidity, and is formed of a non-ferrous alloy such as beryllium copper or nickel bronze, or a material such as super-steel or ceramic. The end portion of the pressurization member 125 is brought into contact with the plane of the test sample 10, and depending on its end portion shape, the force for causing an indentation on the test sample 10 and the way of cracking are different. Therefore, it is preferable that the dimensional shape of the pressurization member 125 is set in consideration of the mechanical properties of the amorphous alloy ribbon, and the intervals of the pressurization portions formed on the test sample 10 are also appropriately considered.

Figure 4:
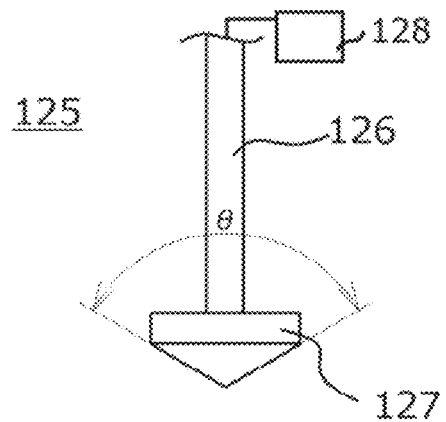
FIG. 4 is a schematic view showing an example of a pressurization member used in the device used for the embrittlement evaluation of the present disclosure.

FIG. 4 is a schematic view showing an example of the pressurization member used in the test device. The illustrated example shows a form having a columnar body portion 126 and a pyramid portion 127 at its end portion. If the end portion of the pressurization member 125 has an acute-angled needle-like shape, it is easy to break through the test sample 10 at once. Therefore, it is preferable that the end portion of the pressurization member 125 has a pyramid shape (conical shape or polygonal pyramid shape). The angle of the weight-shaped tip end (vertex angle θ) is preferably 60° to 130°. A more preferable lower limit is 70° and an even more preferable lower limit is 90°. A more preferable upper limit is 125° and an even more preferable upper limit is 120°. The preferable shape is a hemispherical shape or a conical shape with an obtuse vertex angle, and the diameter dimension of the end portion is preferably φ1.0 mm or more and φ5.0 mm or less.

The pressurization means includes, for example, a force gauge 120 and the pressurization member 125, and is configured by connecting the rod-shaped pressurization member 125 to the force gauge 120 via a fixing means such as a collet chuck. The pressurization means is fixed to a slider of the Z-axis direction drive unit 150 of the test device 100 by bolting or the like. The Z-axis direction drive unit 150 lowers the pressurization means toward the plane of the test sample 10 at a predetermined speed, and presses the tip end side of the pressurization member 125 against the test sample 10 to pressurize. The tip end of the pressurization member 125 descends to a preset position, forms a pressurization portion with an indentation on the test sample 10, and then ascends to a predetermined position by the Z-axis direction drive unit 150 so as to separate from the test sample 10. Next, the pressurization means is moved to a different position on the plane of the test sample 10 by the X-axis direction drive unit 130 and the Y-axis direction drive unit 140, and then formation of the next pressurization portion is repeated for a predetermined number of times. It is preferable that the series of operations of the pressurization portion formation is automatically controlled by a programmable control device. The force (pressurization force) applied to the test sample 10 when the pressurization portion is formed can be measured by the force gauge 120 to which the pressurization member 125 is attached. In the pressurization portion where the test sample 10 is thin and indentation remains, the pressure surface side of the evaluation sample 10 is recessed, and the opposite surface side becomes a protrusion. If the tip end of the pressurization member 125 is hemispherical or an obtuse-angled pyramid, cracks in the pressurization portion are likely to occur from the vicinity of the top portion of the protrusion to the hem.

The pressurization means may be configured to include a load sensor (load cell) 128 and the pressurization member 125. It is also possible to control the pressurization portion formation on the test sample 10 from the pressurization information obtained based on the electric signal from the load cell 128. As the tip end side of the pressurization member 125 comes into contact with the plane of the test sample 10 and descends to a set position, the force (pressurization force) applied to the test sample 10 increases. If a crack occurs in the pressurization portion until the pressurization member 125 reaches a predetermined lowering position, the pressurization force is reduced. The load cell 128 detects such a change in the pressurization force, an electric signal corresponding to the pressurization force applied to the test sample 10 is obtained in pressurization portion formation, and an output of an analog signal from an amplification means for amplifying the electric signal is converted into a digital signal by an AD conversion means and detected, whereby it is possible to determine whether or not a cracks has occurred in the pressurization portion. By an arithmetic processing means, it is also possible to easily obtain data such as the pressurization force distribution in the pressurization portion, the distribution of the pressurization portions in which cracks have occurred, and the number of pressurization portions in which cracks have occurred.

Based on the information from the load cell 128, the tip end side of the pressurization member 125 may be lowered until the force applied to the pressurization portion becomes a preset pressurization force value. When the occurrence of a crack is detected, descending of the pressurization member 125 may be stopped and raised to a predetermined position to move to the next operation of pressurization portion formation.

Figure 5:
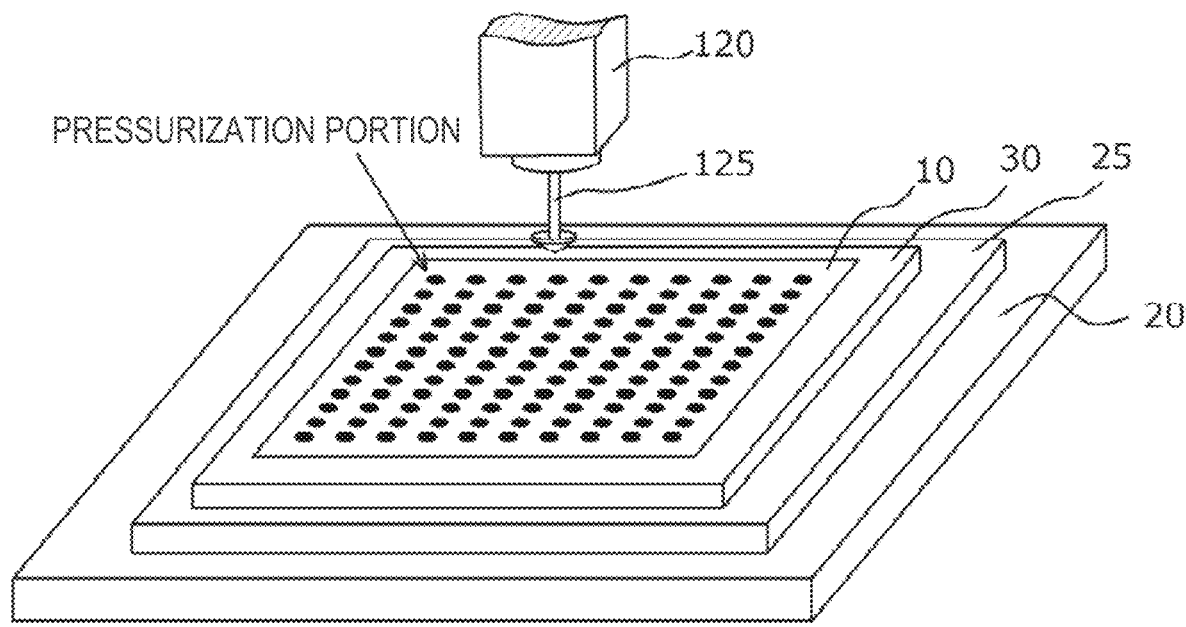
FIG. 5 is a view showing an example of a state in which a test sample is placed on a stage of a device in the embrittlement evaluation of the present disclosure.

FIG. 5 is a view showing an example of a state in which the test sample is placed on the stage of the test device. In the example shown in FIG. 5, a plate-shaped metal base member 20 is placed on the flat stage, and the test sample 10 is placed on a magnetic adsorbent member 25 and an elastic member 30 stacked in this order. The portion indicated by the ellipse painted in black in the test sample 10 corresponds to the pressurization portion of the evaluation sample 10. In order to prevent the base member 20 from moving and the position of the test sample 10 from shifting, it is preferable that a through hole is formed in the base member 20 so as to be able to be fastened and fixed to the stage 110 with screws or the like. In addition to fastening, fixing may be performed by a known means such as clamping or adsorbing. The base member 20 is preferably made of aluminum in consideration of workability, but may be made of steel or stainless steel so that it can be easily fixed to the magnetic adsorbent member 25.

The magnetic adsorbent member 25 is a magnetic adsorbent means (a magnetic adsorbent device) for fixing the test sample 10 by magnetic adsorbent, and is preferably composed of a magnet sheet. If the base member 20 is nonmagnetic, the magnet sheet only needs to be fixed by an adhesive means such as double-sided tape. The test sample 10 has a plate shape with a thickness of equal to or less than several tens of μm at most, but by forming a magnet sheet having a size that covers at least a part, preferably the entirety, of the region for forming the pressurization portion, it is possible to magnetically adsorb and fix the test sample 10 via the elastic member 30 over the entire surface. It is preferable to adjust the adsorbent force by the magnetic force of the magnetic adsorbent means itself or the interval between the magnetic adsorbent means and the test sample 10 for easy removal.

For plastically deforming the test sample 10 to form a pressurization portion having indentation, it is preferable to place the elastic member 30 between the stage 110 and the test sample 10 as an elastic base so as not to hinder the deformation. The elastic member 30 can also absorb and disperse the pressurization force at the time of pressurization portion formation applied to the underlying magnet sheet or the like via the test sample 10.

The elastic member 30 is preferably a sheet of fluororubber or silicon rubber. It is preferable that the size of the elastic member 30 also covers at least a part of the region for forming the pressurization portion of the test sample 10 and further covers the entirety, similarly to the magnetic adsorbent member 25. From the required function, the elastic member 30 preferably has a Shore A hardness of 30 or more and 100 or less, more preferably 35 or more and 90 or less, and yet more preferably 40 or more and 70 or less. The thickness is preferably 0.5 mm or more, more preferably 0.8 mm or more, and yet more preferably 1.0 mm or more. The thicker the elastic member 30 becomes, the more difficult it becomes to obtain the magnetic adsorbent force of the test sample 10 by the magnetic adsorbent member 25, and therefore, the thickness is preferably 3.0 mm or less, more preferably 2.5 mm or less, and yet more preferably 2.0 mm.

Next, a method for confirming the evaluation sample 10 that has undergone the pressurization process will be described. The state of the pressurization portion (presence or absence of a crack) is obtained by observing the indentation, and may be visually evaluated using a magnifying glass or an optical microscope, or the indentation may be observed by an imaging means such as a CCD camera or a CMOS camera and the obtained image data may be image-processed and evaluated.

Figure 6:
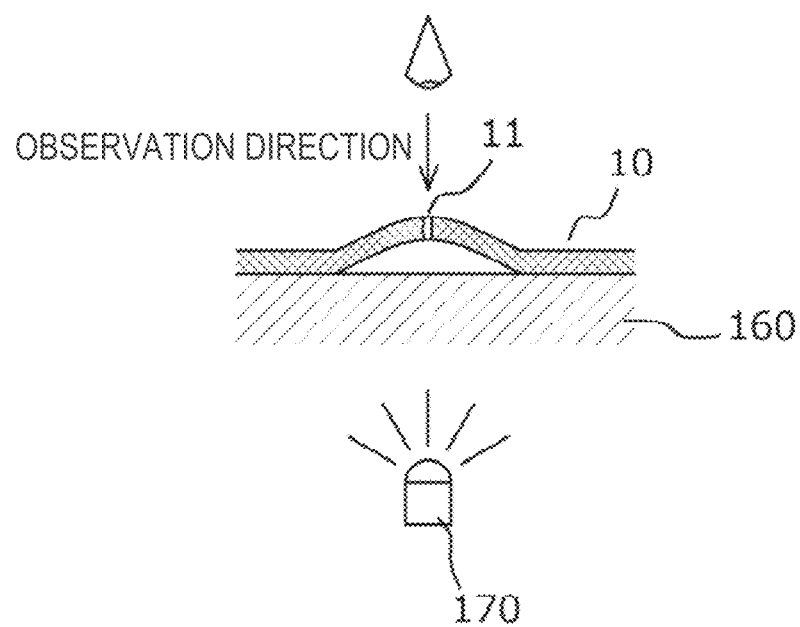
FIG. 6 is a view for explaining an example of a crack confirmation method in a pressurization portion of an evaluation sample in the embrittlement evaluation of the present disclosure.

FIG. 6 is a view for explaining an example of a crack confirmation method. The illustrated example uses a light source device in which a plate of transparent resin or inorganic glass is used as a stage 160, and a light source 170 such as a fluorescent lamp, a halogen light, or a light emitting diode is placed below the stage 160. The evaluation sample 10 is superposed on the stage 160 of the light source device so that the recessed side of the pressurization portion is on the light source 170 side, and light from the light source 170 is transmitted through a crack 11 formed in the pressurization portion of the evaluation sample 10. By placing the light source on the recessed side of the pressurization portion, the transmitted light of the pressurization portion can be clearly confirmed by visual observation from the protrusion side. Furthermore, by observing at a low magnification (typically about 10 to 50 times) using a microscope or a magnifying glass, a part of the crack 11 that shines like a streak with a width becomes clear. Defects such as scratches and holes originally included in the amorphous alloy ribbon can be distinguished from the difference in local light transmission (luminance), the occurrence location, and the difference in the form of crack due to the pressurization portion formation, and fine cracks can also be determined.

It is also preferable to observe the pressurization portion in a state of being magnified using a CCD camera or a CMOS camera and projected onto a monitor. The state of the pressurization portion may be evaluated by performing image analysis. It is found that the degree of crack (severity of damage) occurred in the pressurization portion of the evaluation sample 10 to be observed and the degree of embrittlement correlate with each other. It is also preferable to determine the presence or absence and degree of the crack based on the threshold value by binarizing a captured image, for example, by the arithmetic processing means, quantifying presence or absence of the streak-like pattern portion corresponding to the crack portion and its area. This makes it possible to easily perform the determination, and suppress the variation in determination due to individual differences. By performing data processing on information on the presence or absence of a crack obtained by performing such determination processing for each pressurization portion, it is possible to obtain data such as the distribution of the pressurization portions with a crack in the evaluation sample 10 and the number of pressurization portions with a crack.

The crack may be determined by discontinuity of waviness of the surface shape of the pressurization portion. The waviness of the surface of the pressurization portion of the evaluation sample 10 can be measured in a non-contact manner with a laser microscope or the like.

From the information obtained from the evaluation sample 10, it is possible to evaluate in detail the degree of embrittlement of the amorphous alloy ribbon, and the embrittlement site and its distribution, which are difficult in the conventional tearing tests. It is possible to evaluate embrittlement by, for example, defining, as the degree of embrittlement, the number of pressurization portions per unit area where cracks have occurred, and defining, as the degree of embrittlement, the ratio of the number of pressurization portions where cracks have occurred to the total number of pressurization portions. By evaluating the embrittlement of the as-cast ribbon, it is possible to subdivide the ranking of the as-cast ribbon, and it is possible to use it as a more accurate index of cuttability when cutting and processing the as-cast ribbon. Since it is possible to evaluate the distribution of embrittlement in the as-cast ribbon, it is possible to further rank the ribbon obtained by secondary processing the as-cast ribbon and divided into a plurality of pieces with a predetermined width dimension by a cutting means.

Of course, it is also possible to evaluate embrittlement of amorphous alloy ribbons other than the as-cast ribbon.

EXAMPLES

Example 1

The embrittlement of Fe—Si—B-based amorphous alloy ribbon (2605HB1M manufactured by Hitachi Metals, Ltd.) was evaluated. This amorphous alloy ribbon was 142 mm wide, 26 μm thick, and weighed about 700 kg. The brittle code of JIS C2534 (2017) was 1 (the number of brittle spots in one test piece; 0). The as-cast ribbon was obtained by dividing the amorphous alloy ribbon so that the width became 70 mm. A sample was cut out with a length of 1 m from the as-cast ribbon, and five test samples with a width of 70 mm and a length of 70 mm were cut out from the sample in a discontinuous manner.

Using a 3-axis robot as the test device, a pressurization portion with 313 indentations was formed on the test sample to prepare an evaluation sample. As the 3-axis robot, a tabletop robot TT series manufactured by IAI Corporation was used. A push-pull gauge of Aikoh Engineering Co., Ltd. to which a pressurization member is attached is fastened and fixed to the slider of the Z-axis direction drive unit. The pressurization member includes a columnar body portion and a conical portion having an obtuse vertex angle at its end portion as shown in FIG. 4. The pressurization member used is made of beryllium copper, the body is φ1.4 mm, the conical portion is φ4 mm on the bottom surface, and the vertex angle θ is 120°.

As a base member, an aluminum plate with a thickness of 15 mm was fastened and fixed with bolts to the slider (stage) of the Y-axis direction drive unit of the 3-axis robot, and a commercially available magnet sheet with a thickness of 0.7 mm was stacked and fixed with double-sided tape as a magnetic adsorbent member. As an elastic member, a commercially available silicone rubber sheet was placed on the magnet sheet. A silicone rubber with a thickness of 0.8 mm and a Shore A hardness of 50 was used. A marking was formed on the silicon rubber sheet for positioning for arranging the test samples, and the test samples were placed with reference to the marking to form the pressurization portion. All five test samples were placed on the stage with the casting direction aligned.

Figure 7:
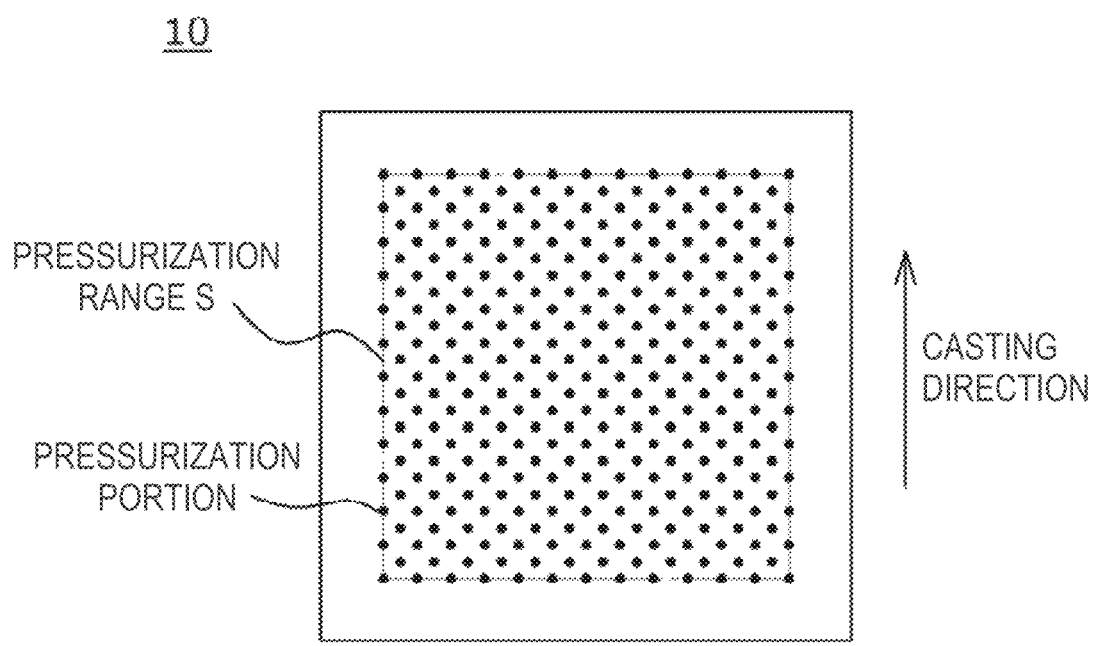
FIG. 7 is a plan view of a test sample used for the embrittlement evaluation of the present disclosure.

A plan view of the test sample is shown in FIG. 7. A plurality of portions indicated by black circles in the figure indicate portions where the pressurization portion is formed. The black circle may be read as the pressurization portion to explain the evaluation sample 10 using FIG. 7. The operation of the 3-axis robot was programmed in advance. The region about 8.3 mm inside from each edge portion of the test sample with a width of 53.5 mm and a length of 53.5 mm was designated to be a range S (region indicated by the thin line connecting the centers of the pressurization portions at the four corners in the figure) to be pressurized. The pressurization portions were formed in a staggered manner at the tip end of the pressurization member so that the interval between adjacent pressurization portions (center interval between the pressurization portions) became 4.46 mm. The operations of the X-axis direction drive unit and the Y-axis direction drive unit were controlled so that 313 pressurization portions were formed per test sample. The pressurization member was lowered to a preset position at 300 mm/s, and the Z-axis direction drive unit was controlled so as to rise from the lowered position to a predetermined position. The position in the Z-axis direction was set so that a pressurization portion with a crack and a pressurization portion without a crack were mixed using a sample for setting conditions obtained from the same as-cast ribbon as the test sample. The pressurization force measured with the force gauge at the pressurization portion without a crack was about 14 N. The pressurization portion was formed under the same conditions for all five test samples to prepare evaluation samples.

Figure 8:
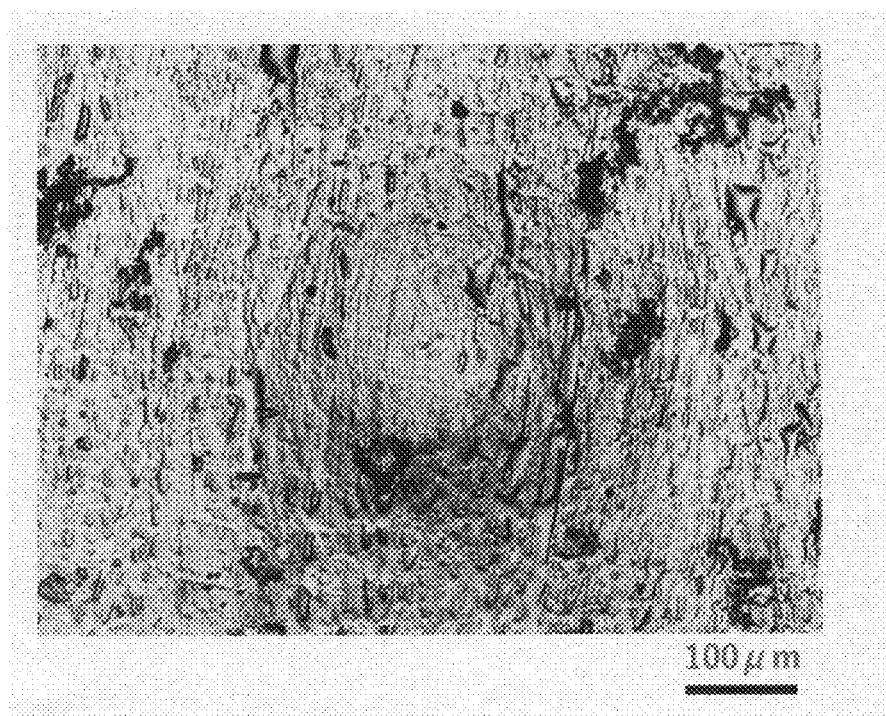
FIG. 8 is an enlarged photograph of a pressurization portion without a crack of an evaluation sample by a laser microscope.
Figure 9:
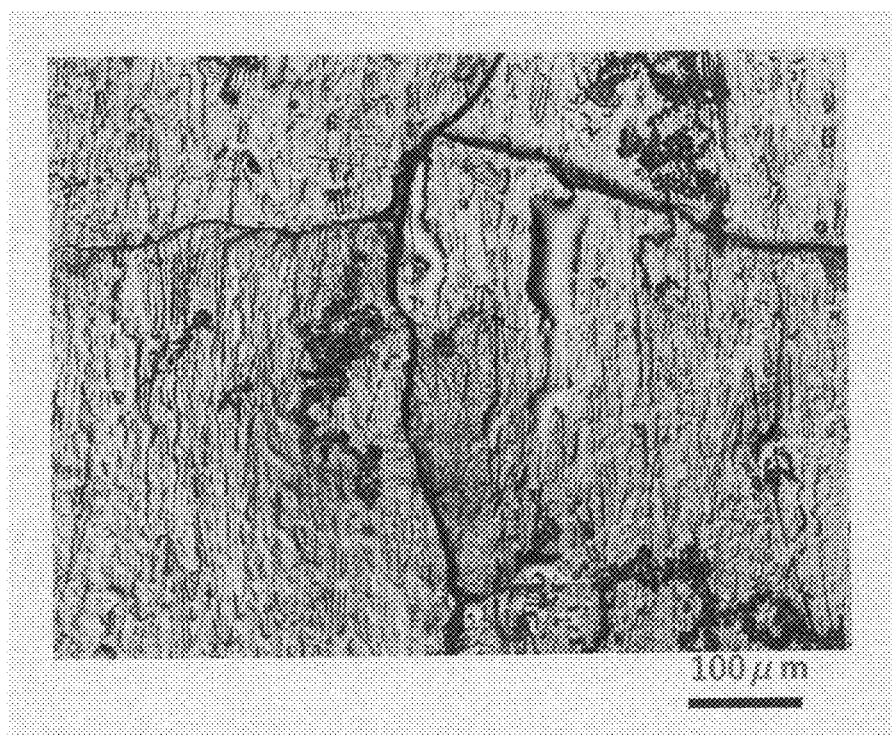
FIG. 9 is an enlarged photograph of a pressurization portion with a crack of an evaluation sample by a laser microscope.
Figure 10:
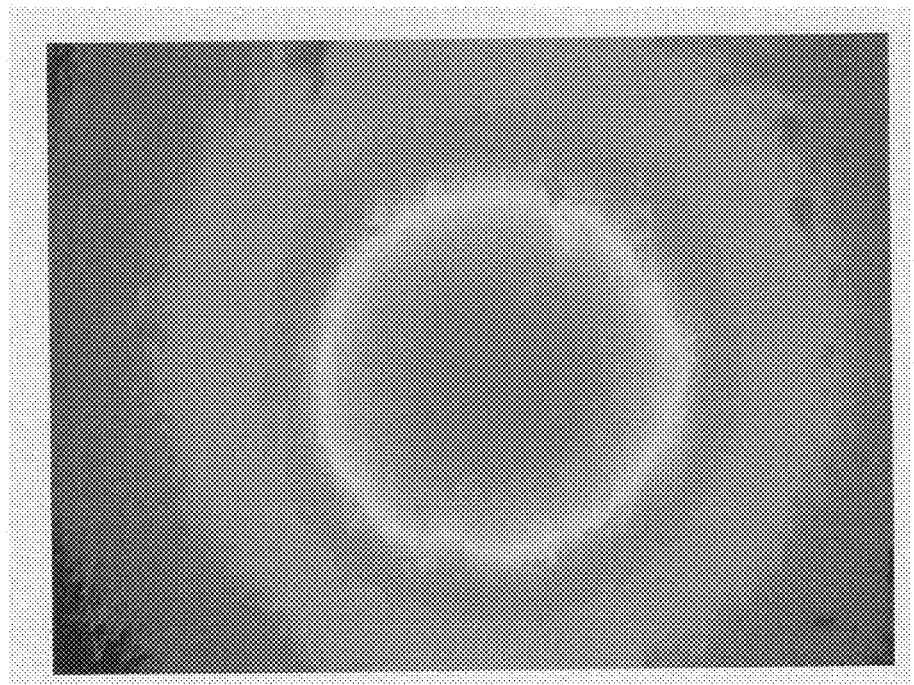
FIG. 10 is a photograph in which waviness of a surface of the pressurization portion in the same field of view as in FIG. 8 is a difference in brightness.
Figure 11:
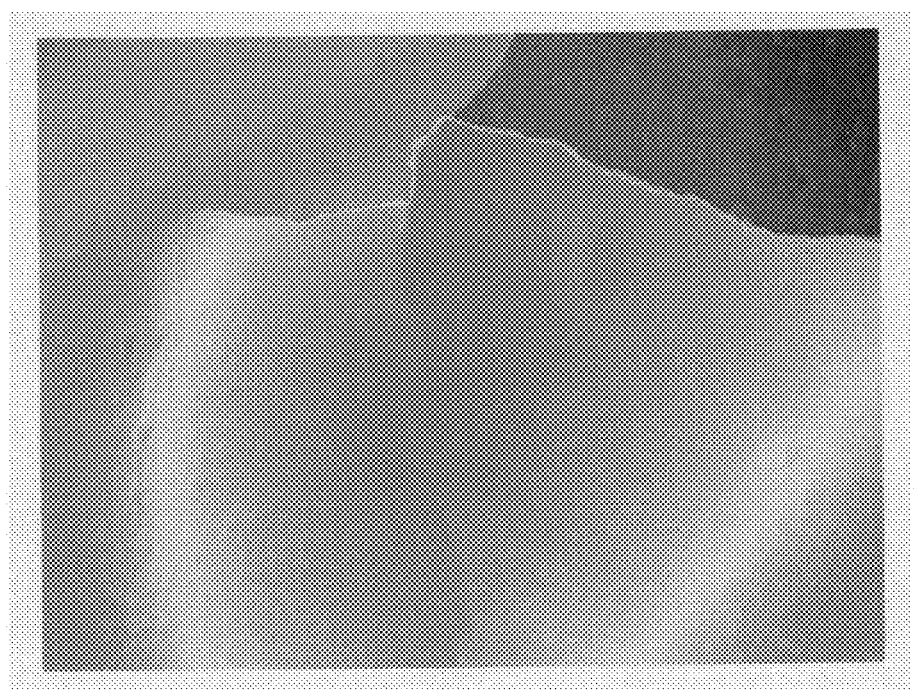
FIG. 11 is a photograph in which waviness of a surface of the pressurization portion in the same field of view as in FIG. 9 is a difference in brightness.

The pressurization portion of the evaluation sample was observed with a laser microscope (VK-X1000 manufactured by Keyence) at a magnification of 20 times for a region of 520 μm×700 μm from the protrusion side to confirm the state of cracking. FIGS. 8 and 9 show enlarged photographs of the pressurization portion by a laser microscope. FIG. 8 is a photograph of the pressurization portion without a crack, and FIG. 9 is a photograph of the pressurization portion with a crack, each of which is shown as a typical form. In the same observation field of view as that in FIGS. 8 and 9, the surface waviness was image-processed and converted into a visually recognizable color tone for confirmation. FIGS. 10 and 11 are photographs in which the waviness of the surface is the difference in brightness. In the pressurization portion without a crack shown in FIG. 10, the waviness on the surface was observed in a halo shape as continuous brightness. On the other hand, in the pressurization portion with a crack as shown in FIG. 11, the cracks run in all directions from the central portion, and in the region defined by the cracks, the waviness of the surface was observed as different brightness.

Next, using a light source device that uses a fluorescent lamp as the light source, the recessed side of the pressurization portion of the evaluation sample became the light source side, and for the 313 pressurization portions, the presence of crack was visually confirmed by the transmitted light transmitted through the crack. The number N of pressurization portions with a crack was measured and recorded in each of the five evaluation samples. The number of pressurization portions with a crack per unit area is defined as the degree of embrittlement (N/S) (pieces/mm$^2$), and the ratio of the number of pressurization portions with a crack with respect to the total number N0 of pressurization portions is defined as the degree of embrittlement (N/N0) (%), as shown in Table 1. The degree of embrittlement (N/S) was calculated by dividing the number N of pressurization portions with a crack by the area (width 53.5 mm×length 53.5 mm) of the pressurization range S to be pressurized.

TABLE 1

| EVALUATION SAMPLE | NUMBER N OF PRESSURIZATION PORTIONS WITH CRACK | DEGREE OF EMBRITTLEMENT (N/S) (PIECES/mm$^2$) | TOTAL NUMBER N0 OF PRESSURIZATION PORTIONS | DEGREE OF EMBRITTLEMENT (N/N0) (%) |
|---|---|---|---|---|
| 1 | 5 | $1.75 \times 10^{-3}$ | 313 | 1.60% |
| 2 | 4 | $1.40 \times 10^{-3}$ | 313 | 1.28% |
| 3 | 3 | $1.05 \times 10^{-3}$ | 313 | 0.96% |
| 4 | 1 | $0.35 \times 10^{-3}$ | 313 | 0.32% |
| 5 | 7 | $2.45 \times 10^{-3}$ | 313 | 2.24% |

The number of pressurization portions with a crack was different depending on the evaluation samples, and the degree of embrittlement for each sheet varied in the casting direction of the amorphous alloy ribbon.

Example 2

Similar to Example 1, the embrittlement was evaluated using a Fe—Si—B-based amorphous alloy ribbon (2605HB1M manufactured by Hitachi Metals, Ltd.). Four amorphous alloy ribbons having different manufacturing lots from the amorphous alloy ribbons of Example 1 were prepared. This amorphous alloy ribbon has a width of 142 mm and a thickness of 26 μm, and each has a weight of about 700 kg. The brittle code of JIS C2534 (2017) is 1 (the number of brittle spots in one test piece; 0). This was used as the as-cast ribbon and cut out with a length of 1.03 m to prepare a test sample having a width of 142 mm and a length of 1.03 m. (Evaluation samples 6 to 9)

The embrittlement was evaluated using a Fe—Si—B-based amorphous alloy ribbon (2605HB1M manufactured by Hitachi Metals, Ltd.) by a process different from the amorphous alloy ribbons from which the evaluation samples 6 to 9 were obtained. The width and thickness were the same as above, and the evaluation sample (evaluation sample 10) was prepared from the as-cast ribbon in the same manner as above.

Using a 3-axis robot for the prepared test sample, similarly to Example 1, a region with a width of 53.5 mm and a length of 53.5 mm was set as the pressurization range S, and the valuation samples were prepared to form 313 pressurization portions per pressurization range S.

Figure 12:
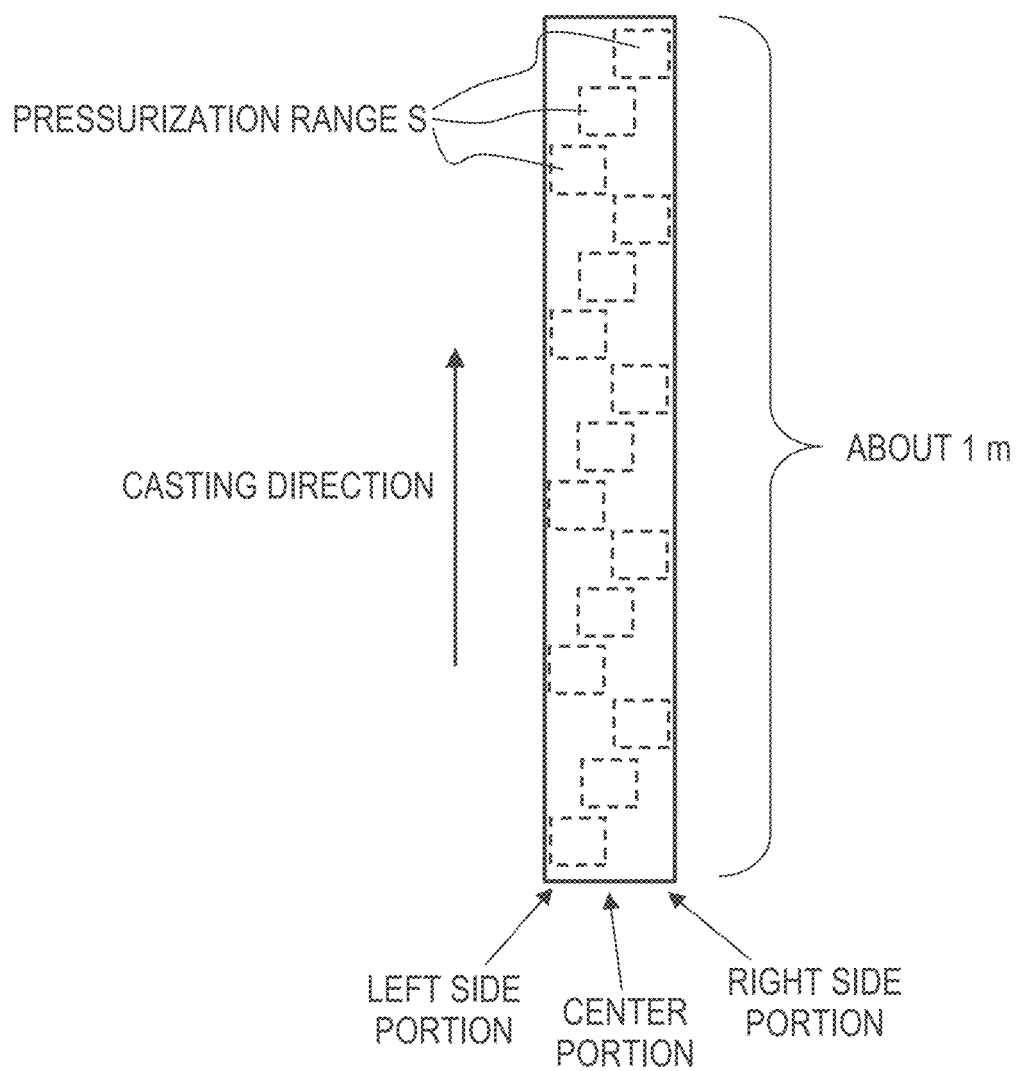
FIG. 12 is a plan view of a test sample used for the embrittlement evaluation of the present disclosure.

As shown in FIG. 12, the region where the pressurization portion is formed (pressurization range S) was about 8.3 mm inward from each edge portion of the test sample. The pressurization portion was formed at five portions each in the casting direction of the as-cast ribbon on the right side and the left side in the width direction of the test sample, and was formed at five portions each in the casting direction of the as-cast ribbon on the central portion in the width direction of the test sample. The interval of the pressurization range S aligned in the casting direction is about 150 mm. The test sample was as long as about 1 m and it was not possible to fit the entire length direction on the stage. Therefore, the test sample was placed on the stage as appropriate and the pressurization portion was formed while changing the position, and the evaluation sample was thus prepared. Since other conditions are the same as in Example 1, the description thereof will be omitted.

Similarly to Example 1, using a light source device that uses a fluorescent lamp as the light source, the presence of crack was visually confirmed by the transmitted light transmitted through the crack. The number M (total of 5 places) of the pressurization portions with a crack was measured and recorded at each of the right side portion, the left side portion, and the center portion of the evaluation sample. The degree of embrittlement was evaluated for the number M (total of 5 places) of the pressurization portions with a crack at each of the right side portion, the left side portion, and the center portion of the evaluation sample, and the number N (total of the three Ms) of pressurization portions with a crack in one evaluation sample. The results are shown in Table 2. The degree of embrittlement was evaluated in the following two ways as the number of pressurization portions with a crack per unit area. First, the embrittlement degree (M/5S) of each of the left side portion, the center portion, and the right side portion was calculated by dividing the number M of the pressurization portions with a crack in each of the left side portion, the center portion, and the right side portion by the total area (5×S) of the pressurization range S. Second, the number N of the pressurization portions with a crack in each overall evaluation sample was calculated by dividing it by the total area (15×S) of the pressurization range S. As for the degree of embrittlement (N/N0), the ratio of the number N of pressurization portions with a crack with respect to the total number of pressurization portions N0 was calculated by N/N0(%). Table 2 also shows the thickness of each as-cast ribbon from which evaluation samples were collected.

TABLE 2

| EVALUATION SAMPLE | THICKNESS ($\mu$m) | PLACE | NUMBER M OF PRESSUR- IZATION PORTIONS WITH CRACK | DEGREE OF EMBRIT- TLEMENT (M/5S) (PIECES/mm$^2$) | NUMBER N OF PRESSUR- IZATION PORTIONS WITH CRACK | DEGREE OF EMBRIT- TLEMENT (N/15S) (PIECES/mm$^2$) | TOTAL NUMBER N0 OF PRESSUR- IZATION PORTIONS | DEGREE OF EMBRIT- TLEMENT (N/N0) (%) |
|---|---|---|---|---|---|---|---|---|
| 6 | 26 | LEFT SIDE PORTION | 24 | $1.68 \times 10^{-3}$ | 59 | $1.37 \times 10^{-3}$ | 4695 | 1.26% |
|   |    | CENTER PORTION | 22 | $1.54 \times 10^{-3}$ |   |   |   |   |
|   |    | RIGHT SIDE PORTION | 13 | $0.91 \times 10^{-3}$ |   |   |   |   |
| 7 | 26 | LEFT SIDE PORTION | 8 | $0.56 \times 10^{-3}$ | 21 | $0.49 \times 10^{-3}$ | 4695 | 0.45% |
|   |    | CENTER PORTION | 6 | $0.42 \times 10^{-3}$ |   |   |   |   |
|   |    | RIGHT SIDE PORTION | 7 | $0.49 \times 10^{-3}$ |   |   |   |   |
| 8 | 26 | LEFT SIDE PORTION | 26 | $1.82 \times 10^{-3}$ | 64 | $1.49 \times 10^{-3}$ | 4695 | 1.36% |
|   |    | CENTER PORTION | 20 | $1.40 \times 10^{-3}$ |   |   |   |   |
|   |    | RIGHT SIDE PORTION | 18 | $1.26 \times 10^{-3}$ |   |   |   |   |
| 9 | 26 | LEFT SIDE PORTION | 15 | $1.05 \times 10^{-3}$ | 49 | $1.14 \times 10^{-3}$ | 4695 | 1.04% |
|   |    | CENTER PORTION | 16 | $1.12 \times 10^{-3}$ |   |   |   |   |
|   |    | RIGHT SIDE PORTION | 18 | $1.26 \times 10^{-3}$ |   |   |   |   |
| 10 | 26 | LEFT SIDE PORTION | 66 | $4.61 \times 10^{-3}$ | 170 | $3.96 \times 10^{-3}$ | 4695 | 3.62% |
|   |    | CENTER PORTION | 27 | $1.89 \times 10^{-3}$ |   |   |   |   |
|   |    | RIGHT SIDE PORTION | 77 | $5.38 \times 10^{-3}$ |   |   |   |   |

The numbers N of the pressurization portions with a crack was different among the evaluation samples, and they were 21 to 170. There were the evaluation sample in which the number of pressurization portions with a crack was different by 10 or more among the left side portion, the center portion, and the right side portion of the evaluation sample.

As shown in Example 1 and Example 2, the embrittlement evaluation method of the present disclosure and the test device used therein can evaluate the embrittlement state in more detail than ever. For example, it can be quantified and evaluated as the degree of embrittlement. This is a new method, and by applying the embrittlement evaluation method of the present disclosure, for example, the as-cast ribbon and the amorphous alloy ribbon obtained by dividing and processing the as-cast ribbon can be further divided according to the degree of embrittlement. The test device for embrittlement evaluation of the present disclosure can be provided at low cost because it can be configured by combining general mechanical devices.

What is claimed is:

1. A method for evaluating embrittlement of an amorphous alloy ribbon, the method comprising:
    pressing a pressurization member from one side to a plurality of positions of an amorphous alloy ribbon, wherein an elastic member is placed on a side of the amorphous alloy ribbon opposite to a surface on which the pressurization member is pressed, so as not to hinder a deformation by the pressurization member;
    scattering, in the amorphous alloy ribbon, pressurization portions where the pressurization member is pressed to form indentation; and
    evaluating embrittlement by the number or distribution of pressurization portions where cracks have occurred.

2. The method for evaluating embrittlement of an amorphous alloy ribbon according to claim 1, wherein the amorphous alloy ribbon is magnetically adsorbed and fixed, and the pressurization member is pressed.

3. The method for evaluating embrittlement of an amorphous alloy ribbon according to claim 1, wherein a crack is discriminated by discontinuity of waviness of a surface shape of the pressurization portion.

4. The method for evaluating embrittlement of an amorphous alloy ribbon according to claim 1, wherein a crack is discriminated from a light transmission state of the pressurization portion.

5. The method for evaluating embrittlement of an amorphous alloy ribbon according to claim 1, wherein a crack is discriminated by a decrease change in pressurization force of the pressurization member.

6. The method for evaluating embrittlement of an amorphous alloy ribbon according to claim 1, wherein the amorphous alloy ribbon is manufactured by continuous casting and the amorphous alloy ribbon at least has a length equal to or greater than a circumference length of a casting roll in the continuous casting.

7. The method for evaluating embrittlement of an amorphous alloy ribbon according to claim 1, wherein the pressurization member comes into contact with the amorphous alloy ribbon and the pressurization member is lowered until a force applied to the pressurization portion becomes a preset value, and when an occurrence of a crack is detected, descending of the pressurization member is stopped and the pressurization member is raised to a predetermined position and the pressurization member is moved to a position of a next pressurization portion.

8. The method for evaluating embrittlement of an amorphous alloy ribbon according to claim 1, wherein a crack is determined by imaging the pressurization portion using a camera, binarizing a captured image, and applying a threshold value to binarized data.

9. The method for evaluating embrittlement of an amorphous alloy ribbon according to claim 1, wherein the elastic member comprises a resin having a Shore A hardness of 30 or more and 100 or less and a thickness of 0.5 mm or more and 3.0 mm or less.

10. A test device for evaluating embrittlement of an amorphous alloy ribbon, the test device including:
    a measurement table including a plane on which an amorphous alloy ribbon is placed,
    an elastic member placed on a side of the amorphous alloy ribbon opposite to a surface on which a pressurization member is pressed, so as not to hinder a deformation by the pressurization member, and
    a pressurization device for pressing the pressurization member from one side to a plurality of positions of the amorphous alloy ribbon and scattering, in the amorphous alloy ribbon, pressurization portions where the pressurization member is pressed to form indentation.

11. The test device for evaluating embrittlement of an amorphous alloy ribbon according to claim 10, the test device wherein the pressurization device can form a crack in at least one of a plurality of the pressurization portions.

12. The test device for evaluating embrittlement of an amorphous alloy ribbon according to claim 10, wherein the pressurization device is positioned above a plane of the measurement table and can move in a substantially perpendicular direction with respect to a plane of the measurement table.

13. The test device for evaluating embrittlement of an amorphous alloy ribbon according to claim 12, wherein the pressurization device is further movable on a plane parallel to the plane of the measurement table.

14. The test device for evaluating embrittlement of an amorphous alloy ribbon according to claim 10, wherein the pressurization member is a rod-shaped member, and the pressurization member is moved in a substantially perpendicular direction with respect to a plane of the measurement table to pressurize the amorphous alloy ribbon with a tip end side of the pressurization member.

15. The test device for evaluating embrittlement of an amorphous alloy ribbon according to claim 14, wherein the tip end side of the pressurization member is curved or pyramid.

16. The test device for evaluating embrittlement of an amorphous alloy ribbon according to claim 15, wherein an end portion of the pressurization member has a predetermined vertex-angle within a range of 60° to 130°.

17. The test device for evaluating embrittlement of an amorphous alloy ribbon according to claim 10, the test device comprising a magnetic adsorbent device for fixing the amorphous alloy ribbon to the measurement table.

18. The test device for evaluating embrittlement of an amorphous alloy ribbon according to claim 10, wherein the pressurization device includes a load sensor.

19. The test device for evaluating embrittlement of an amorphous alloy ribbon according to claim 18, the test device that is configured to be able to detect a crack in the amorphous alloy ribbon from pressurization force information obtained based on an electric signal from the load sensor.

* * * * *